United States Patent [19]

Adler-Nissen et al.

[11] Patent Number: 4,478,854

[45] Date of Patent: Oct. 23, 1984

[54] METHOD OF TREATING PLANT POLYSACCHARIDES

[75] Inventors: Jens L. Adler-Nissen, Gentofte; Henrik Gürtler, Lyngby; Georg W. Jensen, Bagsvaerd; Hans A. S. Olsen, Vanlose; Steen Riisgaard, Vaerlose; Martin Schülein, Kobenhavn, all of Denmark

[73] Assignee: Novo Industri A/S, Denmark

[21] Appl. No.: 491,545

[22] Filed: May 3, 1983

Related U.S. Application Data

[63] Continuation-in-part of Ser. No. 334,329, Dec. 24, 1981.

[30] Foreign Application Priority Data

May 6, 1982 [DK] Denmark ............................. 2025/82

[51] Int. Cl.$^3$ .......................... C12G 1/00; C12H 1/00; C12C 7/00; A23L 2/34
[52] U.S. Cl. ....................................... 426/12; 426/16; 426/46; 426/49; 426/51; 426/52; 435/272; 435/162; 435/93; 435/99
[58] Field of Search ....................... 426/12, 16, 44, 46, 426/49, 51, 52; 435/272

[56] References Cited

U.S. PATENT DOCUMENTS

| | | | |
|---|---|---|---|
| 3,484,255 | 12/1969 | Okada et al. | 435/200 UX |
| 3,640,723 | 2/1972 | Uhlig et al. | 426/46 |
| 4,119,733 | 10/1978 | Hsieh et al. | 426/46 |

OTHER PUBLICATIONS

Derwent Abstract 60536, C/35, (1980), of Belgian Patent No. 882,769.
Kawai et al., Agricultural and Biological Chemistry, vol. 43, (9), 1855–1862, (1979).
Research Disclosure 19314, May 1980.

Primary Examiner—Lionel M. Shapiro
Attorney, Agent, or Firm—Fidelman, Wolffe & Waldron

[57] ABSTRACT

Hydrolysis of plant kingdom polysaccharides by treatment with SPS-ase preparations.

SPS-ase is an enzyme adapted to hydrolyzing the water-soluble protein binding polysaccharide present in soy flour decomposed by use of conventional pectinases, which polysaccharide is believed to be widespread in plant kingdom substances. Treatment with an SPS-ase preparation can clarify juices, wines and beers, hydrolyze process wastes such as sugar beet pulp, pomace, and soy milk remanence, improve the digestability of silage, and reduce the viscosity of wort.

5 Claims, 1 Drawing Figure

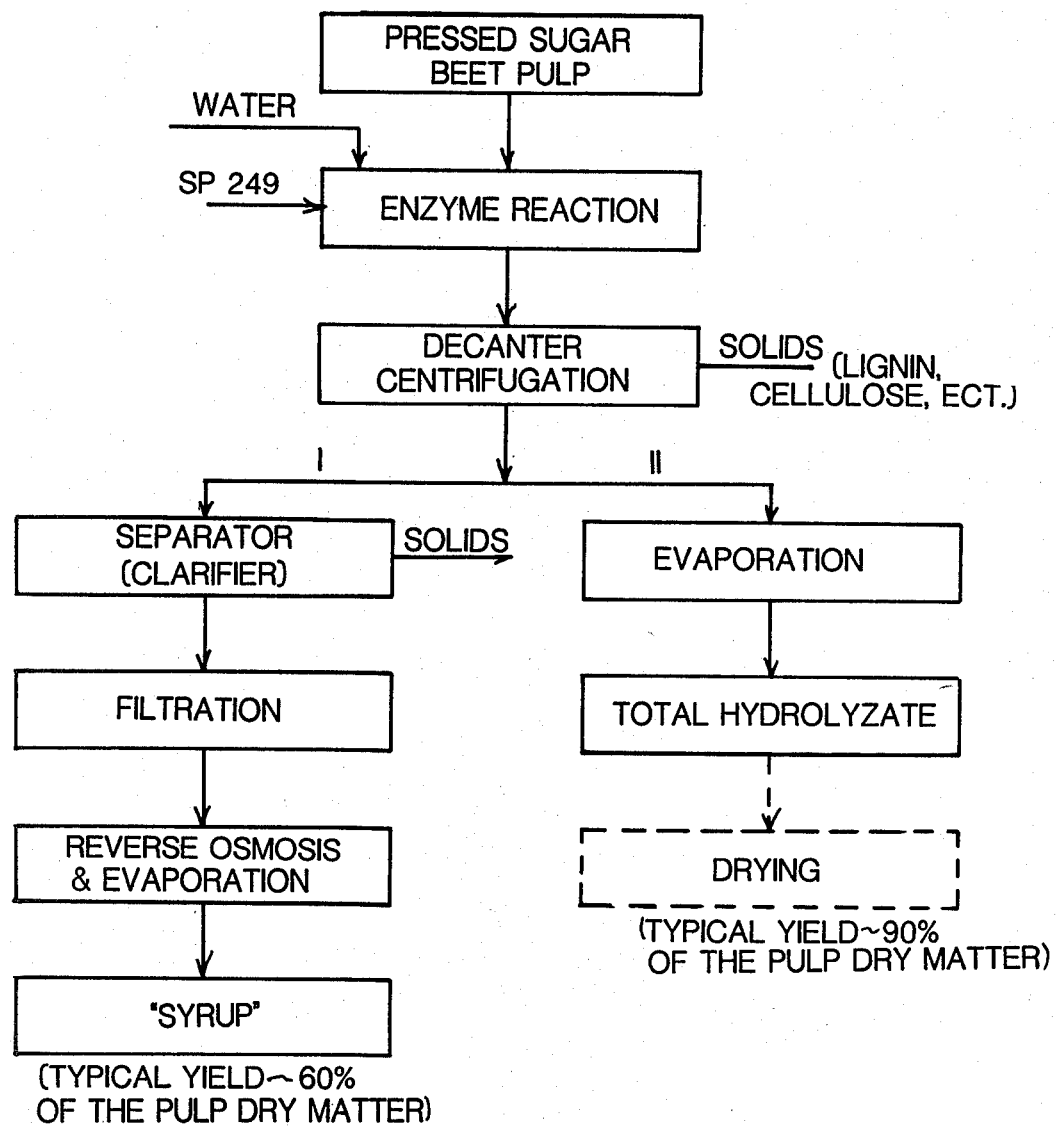

METHOD OF TREATING PLANT POLYSACCHARIDES

This application is a continuation-in-part of Ser. No. 334,329 filed Dec. 24, 1981.

This invention relates to employment of SPS-ase as aid in processing fruits and vegetables into juices, mashes and the like, and in treatment of process wastes.

BACKGROUND OF THE INVENTION

As has been pointed out in some detail by parent applications, Ser. No. 334,329, SPS-ase has the capability of hydrolyzing the water soluble protein binding polysaccharide present in soy flour decomposed by use of conventional pectinases. SPS is characterized by a capability to bind to proteins, and a like or the same water soluble polysaccharide is believed to exist throughout plant kingdom substances.

SPS, as such, has been found to be largely unaffected by treatment with such carbohydrases as pectinases and cellulases. However, SPS-ase purified so as to free from all accompanying enzyme activities has been found to be less effective on SPS than the (more crude) SPS-ase preparations recovered from fermentation of the SPS-ase producing microorganism. In consequence, SPS-ase preparations would normally not be fractionated to provide a single enzyme activity product, nor be treated to destroy the other carbohydrase activities present. SPS-ase preparations recovered from fermentation of an SPS-ase producing microorganism exhibit considerable pectinase activity, cellulase and hemicellulase activity. Some proteinase activity is also present. Presence of a beta-glucanase activity has been found.

The multiple activities present in SPS-ase preparations make such preparations more effective for treatment of SPS itself and make SPS-ase preparations effective hydrolytic enzymes wherever SPS or a like polysaccharide is present, as for example, in juices, mashes, wines, beers and the like, and in some process wastes. Polysaccharides capable of being hydrolyzed by SPS preparations are present throughout the plant kingdom.

An object of this invention is to provide a process for clarifying in juices, wines, beers and the like by treatment with SPS-ase preparations.

A further object of this invention is to improve viscosity characteristics in mashes, worts, and the like by treatment with SPS-ase preparations.

Still another object of this invention is to provide a process for liquefying solid process waste polysaccharide materials by treatment with SPS-ase preparations.

An additional object of this invention is to improve the digestability of silage by treatment of fresh silage with SPS-ase preparations.

BRIEF STATEMENT OF THE INVENTION

In brief, this invention comprises treatment of plant kingdom substances with SPS-ase preparations to hydrolyze polysaccharides therein.

One instance where such a treatment is particularly desirable is for viscosity reduction when starchy plant substances are converted into mash. Wort viscosity is greatly reduced by treatment with SPS-ase preparations.

Another instance where such a treatment is particularly desirable is to improve clarity in liquid products. Treatment of wines, juices, beers with SPS-ase preparations improves clarity by removing components which generate haze.

SPS-ase preparations are applicable to hydrolysis of solid polysaccharide containing process waste residues. For example, sugar beet pulp may be hydrolyzed by treatment with SPS-ase preparations, as can be pomace and soy milk remanence.

Included within practice of this invention is treatment of fresh silage with solutions of an SPS-ase preparation. Digestability of the silage is improved.

DISCUSSION OF THE INVENTION

The SPS-ase preparation enzymes contemplated for practice of this invention are preferably the SPS-ase of *Aspergillus aculeatus* CBS 101.43. CBS is Centraalbureau voor Schimmelcultures, Baarn, The Netherlands. SPS-ase and the SPS-ase preparations herein preferred are described in detail by Ser. No. 334,329 of which this application is a continuation-in-part, reference to parent application, Ser. No. 334,329 being made for full description of this enzyme, its properties and its preparation from the microorganism source thereof.

Presence in SPS-ase preparations of several related carbohydrase activities along with the capability to hydrolyze SPS makes SPS-ase preparations useful for treatment of both liquid and solid plant kingdom substances. SPS or closely related polysaccharides are believed to be widespread in plant kingdom substances.

In some preferred uses such as for wine clarification or for juice treatment wherein the art has heretofore believed that the polysaccharide to be hydrolyzed is particularly susceptible to pectinase, it has now been found that SPS-ase preparations are often superior to pectinases for the clarification purpose.

In other preferred embodiment uses such as mash or wort treatment to reduce viscosity of the wort wherein the polysaccharide to be hydrolyzed has been treated with beta-glucanase heretofore, it has now been found that treatment with SPS-ase preparations result in the viscosity reduction desired in the wort.

The SPS-ase preparations have been found to be quite active for liquefaction of solid polysaccharide containing process residues, such as beet pulp, pomace, and remanence from soy milk production.

The rationale of this invention is treatment with SPS-ase preparations as an adjunct to existing state-of-the-art foodstuff processes without fundamental change in the process. Thus, in clarifying juices, wines, beers, SPS-ase would be substituted for the prior art enzymes (e.g. pectinase) employed. For viscosity reduction in wort, SPS-ase would be substituted for beta-glucansase. For liquefaction of solid process wastes such as sugar beet pulp, pomace, soy milk remanence by treatment with SPS-ase preparations, the liquefaction would be carried out subsequent to the state-of-the-art process which generates the solid waste material. It is recognized, however, that availability of SPS-ase preparations may make fundamental changes in state-of-the-art processes possible.

The inventors hereof have been made aware of process improvements based upon use of SPS-ase preparations. Thus, reference is made: to copending application, Ser. No. 491,892 filed concurrently herewith for details of a process to recover juice from pomace; to copending application, Ser. No. 491,184, filed concurrently herewith for details of a process to convert soy four to soy milk and to prepare a protein product suited to use in milk substitutes; and to Ser. No. 491,183 filed concurrently herewith for a process to recover instant tea from tea leaves.

Throughout many of the various specific uses for SPS-ase preparations herein described and exemplified extends a likelihood that SPS or a closely related polysaccharide is present in he substrate substance and that such polysaccharide renders the pectin, beta-glucan, etc. relatively inaccessible to the pectinase, beta-glucanase, etc. heretofore employed by the art to clarify wines or reduce visocisty of wort, etc. To the extent pectinase activity as such, beta-glucanase activity as such, etc., is required to hydrolyze the substrate, some of each such activity is present in SPS-ase preparations, usually enough to meet the needs of the substrate. Of course, the activity of pectinase or beta-glucanase, etc. present in the SPS-ase preparation provides far less unit proportions than would be present if a pectinase or beta-glucanase, etc. treatment were being given.

Parenthetically, it is recognized that an alternative reason for the postulated, almost universal applicability of SPS-ase preparations for hydrolysis of plant kingdom substances might well be that hitherto unrecognized carbohydrases activities present in SPS-ase preparations render the SPS-ase preparations active in instances where SPS or a closely related polysaccharide are not present in the plant kingdom substance. In any event, SPS-ase preparations are believed to be applicable for treatment of plant kingdom substances in a generic sense. The widespread applicability of SPS-ase preparations is illustrated and exemplified by the diverse uses detailed hereinafter, which uses constitute preferred embodiments of this invention and of practice thereof.

SILAGE TREATMENT

It is known to add enzymes to fresh silage in order to increase the rate of the silage process and the digestability of the silage. It has been found that treatments with solutions of SPS-ase preparations are superior in comparison to known enzymatic silage aids.

Although at the data hereof no detailed data is available to employment of aqueous SPS-ase preparation on fresh silage, considerations recognized by the art as important to use of any particular enzyme for treatment of silage are sugar release capability and the cellulase activity therein. SPS-ase preparations are powerful cellulases, as is demonstrated by an example herein, wherein the action of the SPS-ase preparation KRF-68 and of a commercial cellulase (Celluclast ®) from *Trichoderma reesei* on crystalline cellulose are compared. In addition a significant sugar release capability is demonstrated by the following example.

EXAMPLE 1

Two Erlenmayer flask each containing 15 g of lawn grass (24.6% dry matter) (from the garden of an inventor hereof) was cut to pieces of one (1) cm. 75 ml of citrate puffer (pH=4.5) was added. 0.03 g of penicillin + 0.03 g of Streptomycin was added for securing of microbial stability.

To one of the flasks an enzyme dosage of 0.073% w/w of SPS-ase (batch 1340) was added. The two flasks were incubated in a vibrating bath at 20° C. for 72 hours. Samples were drawn at 24, 48, and 72 hours. The samples were filtered and analysed for total sugar and the following results found:

| Incubation time hours | Total sugar % | |
|---|---|---|
| | blank | SPS-ase treatment |
| 24 | 0.24 | 1.6 |
| 48 | 0.16 | 1.9 |
| 72 | 0.13 | 1.1 |

A significant almost immediate release of sugar results when SPS-ase is incorporated in the incubation mix.

EXAMPLE 1-A

Avicel, a crystalline cellulose material, was suspended in water (20% dry matter); pH was adjusted to 5, and the temperature was maintained at 50° C. After 24 hours reaction time, the slurry was filtered, and the content of reducing sugar (mg glucose/g AVICEL) was measured. Using enzyme dosages of 5% and 20% of the cellulose content, the following values were found.

TABLE I

| Enzyme | E/S % | mg glucose/g AVICEL |
|---|---|---|
| Celluclast$^{(R)}$ | 5 | 80 |
| SPS-ase | 5 | 200 |
| Celluclast$^{(R)}$ | 20 | 100 |
| SPS-ase | 20 | 340 |

LIQUEFACTION OF PROCESS WASTES

Processing of many plant kingdom substances into foodstuffs generate large quantities of clean, water-wet, polysaccharide-containing waste products. Grapes are converted into pomace and into must or grape juice. Oranges and grapefruits are converted into citrus juice and citrus rind, the rind being a pomace. Apples and pears are converted into juice and pomace. Sugar beets are converted into sugar juice or molasses and beet pulp. Although it is recognized that the solid by-products of such processing often have commercial utility (for animal foodstuff purposes mostly) these by-products are herein categorized as process waste materials. Liquefaction of plant kingdom process waste materials with SPS-ases is explicitly contemplated for practice of this invention, and is exemplified below by liquefaction of beet pulp and of soy milk remanence.

EXAMPLE 2

Ten (10) kg of pressed sugar beet pulp (about 23% dry matter) obtained from continuous countercurrent extraction of sugar beet cossettes in a DDS-diffuser at Nakskov Sugar Factory was milled twice in a Fryma mill (type MZ-110). Processing water was added during the milling operation.

300 g portions of the pulp were now enzyme treated at 45° C. for eighteen (18) hours by means of the enzyme dosages shown in Table II-A. The dry enzyme product (KRF-68) was added to the pulp which was stirred by a rod during the first hour. Thereafter, the pulp was liquefied to such an extent that magnet stirring could successively be performed for the remaining time. At the end of the reaction pH was measured (no pH-corrections were made during the start of the reaction) and the reaction mixture was centrifuged until a clear supernatant was obtained. Dry matter determinations were performed on the reaction mixtures and on the supernatants. Based on these results the percentage of solubilized dry matter were calcuulated. Corrections for the soluble dry matter of the enzyme product were made in all calculations.

Supernatants Nos. 2, 3, and 4 were ion exchanged and analyzed by HPLC for carbohydrate composition. The data has been tabulated in Table II-B.

TABLE II-A

Results obtained by enzymatically liquefaction of beet pulp.

| Experiment No | Enzyme dosage in relation to dry matter, E/S % | Final measurements | | | |
|---|---|---|---|---|---|
| | | Reaction mixture | | Supernatants | |
| | | pH (final) | % dry matter | % dry matter | % solubilized dry matter |
| 1 | 0 | 5.5 | 4.18 | 0.0 | 0.0 |
| 2 | 0.35 | 3.6 | 3.85 | 2.58 | 66.9 |
| 3 | 0.56 | 3.5 | 3.81 | 2.56 | 66.2 |
| 4 | 1.02 | 3.5 | 3.86 | 2.73 | 70.4 |
| 5 | 1.58 | 3.3 | 3.17 | 2.34 | 73.4 |
| 6 | 3.10 | 3.4 | 3.23 | 2.49 | 76.4 |
| 7 | 7.52 | 3.4 | 2.66 | 2.18 | 80.5 |

Reaction conditions:
M = 300 g
S = 4.18% dry matter
E/S as shown above
pH not adjusted
T = 45° C.
t = 18 hours

TABLE II-B

| | HPLC Data. | | |
|---|---|---|---|
| | Experiment No. | | |
| Sugar type (Neutral) | 2 | 3 | 4 |
| | % of neutral sugars | | |
| High molecular (DP4+) | 43.6 | 31.9 | 25.3 |
| Disaccharides | 4.6 | 4.8 | — |
| Glucose | 20.4 | 23.7 | 27.8 |
| Galactose | 5.0 | 5.9 | 7.3 |
| Fructose/Arabinose | 26.4 | 32.2 | 33.2 |
| Galacturonic acid | not measured | | |

EXAMPLE 2A

Sugar beet pulp liquefaction and saccharification.

The enzymatic reaction step has been studied broadly in the laboratory for optimization. Over the period the SPS-ase batches SP 249 (KRF-68) and SP249 (PPS 1394) were used. The optimum reaction parameters were found to be the following for the combined liquefaction and saccharification process:

| Substrate conc. | 7% dry matter |
|---|---|
| Temperature, T | 45° C. |
| SP 249 dosage | E/D = 0.2% KRF-68 (on dry matter) |
| | E/D = 4.0% PPS 1394 (on dry matter) |
| Time, t | 48 hours |
| pH | decrease from 5.5–3.5 |

Two types of products have been produced. The one may be characterized as the totally liquefied pulp (total hydrolyzate) and the other as the "syrup".

Reference is made to the attached drawing (FIG. 1) for the flow sheet of the two products, which products are believed suited to animal feed purposes. The compositions are tabulated below.

| | "Syrup" (Process I) | "Total hydrolyzate" (Process II) |
|---|---|---|
| Dry matter % | 40.8 | 14.8 |
| Nitrogen % | 0.5 | 0.2 |
| Ash % | 4.6 | 1.0 |
| Fibre % | 0 | 2.0 |
| Cellulose % | 0 | 2.5 |
| Pentosan % | 0 | 3.2 |
| Lignin % | 0 | 0.4 |
| Reducing Sugar % | 25.0 | 4.0 |
| Galacturonic acid % | 9.0 | 5.9 |
| Glucose % | 3.2 | 0.1 |
| Xylose + Galactose % | 2.1 | 0.3 |
| Arabinose % | 8.1 | 0.8 |
| $DP_2$ % | 3.7 | 0.4 |
| $DP_{4+}$ % | 7.9 | 2.1 |
| Batch No. | APR-08 | APR-6A |

EXAMPLE 3

In a traditional production of soy milk, soy beans are soaked in boiling water, milled and extracted with hot water, whereafter a separation is carried out. The water insoluble residue from this separation is the material used for the experiment of this Example. The liquid phase is the soy milk, which may be further treated to produce tofu.

Ten (10) kg of whole soy beans obtained from Aarhus Oliefabrik A/S was milled simultaneously with seventy (70) liters of boiling water in a Fryma mill type MZ 110. The milled slurry was then held above 85° C. for fifteen (15) minutes in order to inactivate the natural bean enzymes which develop the well-known soy bean off-flavor. Five (5) liters of this soy bean slurry was then centrifuged in the laboratory for fifteen (15) minutes at $3000 \times g$ (g=gravity). It was found by analysis that the remanence, as separated out, contained 20.45% and 20.06% dry matter (duplicate determinations, calculated average 20.26%). HCl (6N) was slowly added and worked into the remanence with a spatula until a pH-meter showed pH 4.50, when the electrode was introduced directly into the mass.

Enzyme reactions on $2 \times 200$ g of the mass with the two dosages of the SPS-ase (KRF-68) E/S=0.5% in relation to dry matter and E/S=3.0% in relation to dry matter were carried out in a 500 ml beaker at 50° C. The dry enzyme was added to the mass. During the first 1 to 2 hours, the stirring was carried out with a spatula and hereafter the mass was liquefied to such an extent that stirring with a magnet could be carried out successfully. The total reaction time was 21 hours. During the reaction, the osmolality was measured with an osometer (Advanced Digimatic 3DII from Advanced Instruments, Inc.). The results in Table III show the course of the reaction. At the end of the experiment, the mixtures were centrifuged at $3000 \times g$ for fifteen (15) minutes. A layer of oil appeared on the top of the supernatants and the volume thereof was determined. A loose sludge appeared as a bottom-layer. The supernatant including the oil was removed with a pipette. The oil was combined with the clear water phase by homogenization and a sample was drawn for dry matter determinations. The results shown in Table III clearly demonstrate that the soy milk remanence can be liquefied by treatment with SPS-ase preparation.

TABLE III

Results obtained during liquefaction of soy milk remanence-sludge.

| Reaction conditions and results | Experiment A | | | Experiment B | | |
|---|---|---|---|---|---|---|
| Mass of residue | 200 g | | | 200 g | | |
| Mass of SPS-ase (KRF-68) | 0.20 g | | | 1.20 g | | |
| Temperature | 50° C. | | | 50° C. | | |
| pH | 4.50 | | | 4.50 | | |
| Reaction time | 21 hours | | | 21 hours | | |
| Results measured on osmometer during the course of the reaction. | t min. | osmolality sm | Δ osmolality sm | t min. | osmolality sm | Δ osmolality sm |
| Δ Osmolality is the value corrected for the osmolality of the mixture at t = 0 | 0 | 287 | 0 | 0 | 282 | 0 |
| | 10 | 313 | 26 | 10 | 368 | 86 |
| | — | — | — | 25 | 497 | 215 |
| | 40 | 391 | 104 | 45 | 601 | 319 |
| | 95 | 501 | 214 | 95 | 718 | 436 |
| | 250 | 634 | 347 | 250 | 875 | 593 |
| | 1260 | 907 | 620 | 1260 | 1145 | 863 |
| Reaction mixture: Dry matter | 20.3% | | | 20.7% | | |
| Supernatant: Dry matter | 18.0% | | | 19.4% | | |
| Supernatant: Oil content | 8–10% | | | 8–10% | | |
| Calculation % solubilized dry matter | 88.6% | | | 93.5% | | |

Starchy Substances

A special class of plant kingdom substances that may be treated with SPS-ase preparations advantageously are the starchy substances. Within the context of this invention, inulin containing substances, such as Jerusalem artichokes, are considered to be starchy substances.

Typically, the starch substances is subjected to a mashing process, producing a wort. The wort is then fermented into a beer. Often, the wort is of excessively high viscosity and treatment with enzymes, such as beta-glucanase has been suggested to solve viscosity problems. Treatment with SPS-ase preparations, which treatment may be at any stage of the mashing process results in a reduced viscosity wort.

EXAMPLE 4

From fresh and grated sweet potatoes (Japanese) a mash with a dry matter content of 24% was produced. The starch content of sweet potatoes was found to be approximately 70% of the dry matter content thereof. A preliquefaction treatment with bacterial amylase, Thermamyl ® 60L in dosage of 0.5 kg/ton of starch was performed by heating the mash to 90° C. The mash was then held at 90° C. for thirty (30) minutes. The viscosity of the reaction mixture was then measured by means of a HAAKE spindle at 90° C.

The reaction mixture was cooled to 55° C., and adjusted to pH 5.0 with 2N $H_2SO_4$. A saccharification was then initiated by addition of the gluco-amylase, SAN 150 (NOVO INDUSTRI A/S) in dosage of 1.75 liter/ton of starch. The saccharifying mixture was promptly divided into three parts, A, B, and C, which were enzyme treated for fifteen (15) minutes as described below before measurement of viscosity was made:
  A. The control.
  B. The *Tricoderma reseei* cellulase, Celluclast-® — 200N was added in dosage of 1 kg/ton of dry matter of the sweet potatoes.
  C. The SPS-ase preparations KRF-68 was added in dosage of 0.25 kg/ton of dry matter of the sweet potatoes.

The test results are tabulated below.

TABLE IV

| | VISCOSITIES | |
|---|---|---|
| Reaction mixture | Viscosity at 90° C. | Viscosity at 55° C. |
| Pre-liquefied sweet potatoes | $\gamma_1 = 770$ cp | $\gamma_2 = 2190$ cp |
| A | — | $\gamma_2 = 2190$ cp |
| B | — | $\gamma_3 = 1970$ cp |
| C | — | $\gamma_4 = 950$ cp |

Thus, it can be seen that the viscosity of the reaction mixture could be effectively reduced with the SPS-ase in a low dosage compared to the Celluclast ®

EXAMPLE 5

The production of ethanol by fermentation starting with the inulin containing Jerusalem artichoke was examined in laboratory scale with simultaneous saccharification by SPS-ase and inulinase and four different pretreatments of the Jerusalem artichokes.

SPS-ase: The SPS-ase preparation KRF-68 was used.
Inulinase: The inulinase was produced by fermentation of Asp. ficuum (CBS 55 565). The inulinase activity (covering both endo and exo activity) is determined in the following manner:

Substrate: 5% inulin in acetate buffer (0.1M) pH 4.7
Incubation: 1 ml substrate + 1 ml enzyme 20 min., 50° C.
Stop reagent: 4 ml 0.5N NaOH.

The released reducing sugars (fructose and a small amount of glucose) are determined quantitatively by means of the Somogyi-Nelson method, vide Journal of Biological Chemistry, Vol. 153, page 375–380, 1944.

One inulinase activity unit is defined as the amount of enzyme which is able to form one micromole reducing sugar per minute under the above indicated conditions.

Laboratory Fermentation 150 g portions of the mash were fermented at 30° C. after addition of 4.5 g of bakers yeast and 1 ml of a 4% solution of Pluronic as an antifoaming agent. The fermentation flasks are provided with $CO_2$ traps containing 98% sulphuric acid, and the fermentation is followed by measurement of the weight loss due to evolution of the liberated $CO_2$. The content of the flasks is agitated. Three flasks were used for each parameter studied.

In the results herein tabulated, the weight loss due to liberation of $CO_2$ is converted to ethanol produced assuming that 1 mol liberated $CO_2$ is equivalent to 1 mol $C_2H_5OH$

Pre-treatments of the Artichokes

Treatment A 14.1 kg artichokes (22.8% dry matter) was Henze-cooked at 140° C. and 4–5 atm. for twenty (20) minutes. The weight after cooking was 19.0 kg (16.9% dry matter). Fermentations were performed directly on the mash.

Treatment B

Washed and sliced artichokes were mixed with water (1:1) and blended in a Waring blender. The mash was then heat treated for one (1) hour at 85° C. and pH=4.5.

Treatment C

As in B, but pH was not adjusted.

Treatment D

As in B, but no heat treatment and no pH adjustment.

Results

The results tabulated below show the effect addition of SPS-ase to the pretreated mash has on the ethanol yield. A consistent improvement in ethanol yield was obtained when SPS-ase was added.

TABLE V

Fermentation results from simultaneous fermentation and enzyme saccharification of Jerusalem artichokes.

| Pre-treat-ment | Inulinase units added to 1 g of dry matter | SPS-ase E/S % | Loss of $CO_2$ (g) after 42–44 hours of fermentation | % ethanol produced in relation to dry matter |
|---|---|---|---|---|
| A | 1.5 | 0    | 7.65 ± 0.05 | 31.5 |
|   | 1.5 | 0.27 | 8.07 ± 0.08 | 33.2 |
| B | 1.5 | 0    | 4.85 ± 0.03 | 29.7 |
|   | 1.5 | 0.40 | 5.41 ± 0.03 | 33.1 |
| C | 1.5 | 0    | 5.70 ± 0.05 | 34.8 |
|   | 1.5 | 0.10 | 5.97 ± 0.01 | 36.5 |
|   | 1.5 | 0.20 | 6.13 ± 0.06 | 37.5 |
|   | 1.5 | 0.30 | 6.13 ± 0.00 | 37.5 |
|   | 1.5 | 0.40 | 6.18 ± 0.05 | 37.8 |
| D | 1.5 | 0    | 5.77 ± 0.02 | 35.3 |
|   | 1.5 | 0.10 | 5.89 ± 0.00 | 36.0 |
|   | 1.5 | 0.20 | 6.04 ± 0.11 | 36.9 |
|   | 1.5 | 0.30 | 6.01 ± 0.01 | 36.7 |
|   | 1.5 | 0.40 | 6.02 ± 0.03 | 36.8 |
|   | 0   | 0.40 | 5.48 ± 0.02 | 33.5 |

Mashing Adjunct for the Beer Arts

In production of beer non-starch carbohydrates in the raw materials, e.g., the beta-glucans of malt and barley, influence the viscosity and filterability of the wort. Addition of SPS-ase during mashing reduces wort viscosity and improves filterability and extract yield. Furthermore, addition of SPS-ase during mashing marginally increases both the fermentability of the wort, and the nitrogen content in the wort.

EXAMPLE 6

In the laboraory 50 g of milled grits consisting of 50% malt and 50% barley were mashed with 275 g of water (15% dry matter) according to the following mashing diagram:

52° C. (60 min.)/63° C. (60 min.)/76° C. (30 min.)

In order to demonstrate the effect on an SPS-ase preparation four tests were carried out on mashes made as described above vide Table VI for enzymes and dosages. The enzymes were added during mashing (pH of mash 5.5–6.0). The results are tabulated below.

TABLE VI

| Enzyme | Control | Cereflo(R) | SPS-ase (KRF-68) | |
|---|---|---|---|---|
| Activity of beta-glucanase/g | 0 | 200 BGU | 1630 FBG | 1630 FBG |
| Dosage of enzyme per kg grits | 0 | 1.5 g | 0.05 g | 0.18 g |
| Total dosage of enzyme activity units per kg grits | 0 | 300 BGU | 80 FBG | 300 FBG |
| Filtration rate of wort after 10 minutes | 120 ml | 135 ml | 160 ml | 170 ml |
| Viscosity of wort 10° Balling (25° C.) | 1.52 cP | 1.36 cP | 1.36 cP | 1.30 cP |

BGU is beta-glucanase units determined according to analytical method AF 70/4-GB obtainable from NOVO INDUSTRI A/S.

FBG is fungal beta-glucanase units determined according to analytical method AF 70.1/2-GB obtainable from NOVO INDUSTRI A/S.

The only difference between BGU and FBG is the pH at which the enzyme determination is carried out: pH 7.5 for BGU and pH 5.0 for FBG.

Cereflo is a bacterial beta-glucanase preparation described in the information leaflet B 214b-GB 1500 July 1981 available from NOVO INDUSTRI A/S.

EXAMPLE 7

In the laboratory 50 g of milled grits consisting of 40% malt and 60% barley were mashed together with 150 g of water (25% dry matter) according to the following mashing diagram:

45° C. (60 min.)/63° C. (90 min.)/75° C. (15 min.)

In order to demonstrate the effect of an SPS-ase preparation three tests were carried out on mashes made as described above, vide Table VII for enzymes and dosages. The enzymes were added during mashing (pH of mash 5.5–6.0). The results are tabulated below.

TABLE VII

| Enzyme | Control | Ceremix(R) | Ceremix(R) + SPS-ase (KRF-68) |
|---|---|---|---|
| Activity of beta-glucanase/g | — | 200 BGU | 200 BGU + 1630 FBG |
| Dosage of enzyme per kg grits | — | 1.65 g | 1.65 g + 0.033 g |
| Total dosage of enzyme activity units per kg grits | 0 | 330 BGU | 330 BGU + 50 FBG |
| Filtration rate of wort after 30 minutes | 48 ml | 98 ml | 111 ml |
| Extract, °Balling | 18.6 | 19.0 | 19.5 |
| Viscosity of wort 10° Balling (25° C.) | 1.72 cP | 1.37 cP | 1.27 cP |

The definition of BGU and FBG is as described in Example 6.

Ceremix® is a bacterial beta-glucanase preparation described in the information leaflet B 216 b-GB 1000 February 1982 available from NOVO INDUSTRI A/S.

Treatment of Beers and Juices

SPS-ase can be added during fermentation of wort or storage of beer in order to reduce the content of beta-glucans and thereby improve beer filtration and also beer stability in regard to haze. SPS-ase will also exert an effect on the substances responsible for chill haze. In regard to treatment of a liquid such usage for SPS-ase preparations is similar to the usage in juices as exemplified below.

After production of clear apple juice or pear juice and other fruit juices which juices are previously treated with conventional pectinase and arabanase preparations in order to prevent formation of turbidity, an apple haze or similar fruit hazes may appear. It has been found that the SPS-ase preparations are well suited for decomposition of such hazes.

EXAMPLE 8

Pear juice concentrate produced by enzymatic liquefaction of pear cannery waste using Celluclast ® and Pectinex ® was found to be cloudy on standing. The haze was isolated and hydrolyzed with 0.01N $H_2SO_4$ for 24 hours and analyzed by HPLC. The chromatogram showed arabinose and small amounts of oliogosaccharides.

By incubation of 0.5% w/v of this isolated carbohydrate in 1 mM acetate buffer at pH 4.5 for three (3) hours at 40° C. with a mixed SPS-ase preparation (KRF-68+KRF-92 1:1) at an enzyme concentration of 0.05% w/v it was found that 84% of the initial haze carbohydrate (dry matter) was converted to arabinose.

Also diluted pear concentrate (20° Brix) was treated for two hours at 40° C. with an enzyme dosage of the above mentioned SPS-ase preparation of 0.15% w/v or with a commercial pectinase product called Clarex ® in a dosage of 1% w/v. It was found that the SPS-ase reduced the relative HPLC peak area of an araban-like haze by 86%, whereas the corresponding reduction with Clarex ® (used in higher proportion dosage than the SPS-ase preparation) was only 78%.

In industrial practise it was found that a satisfactory haze reduction was obtained if the SPS-ase preparation was added to the whole, crushed pears in a concentration corresponding to between 1 and 100 SAE/kg of whole pears, preferably around 10 SAE/kg of whole pears, if the treatment time was at least 2 hours and the treatment temperature was around 40° C.

It has been found that white wines exhibiting a highly undesired turbidity can be clarified by means of SPS-ase. It has been shown that the cloudy material mainly consists of polysaccharides containing arabinose and galactose which are bound to hydroxypoline residues in a cell wall structural protein.

We claim:

1. A process for hydrolyzing plant kingdom polysaccharides which comprises treating a polysaccharide containing plant kingdom substance with an SPS-ase preparation, said SPS-ase being characterized as capable of degrading the water-soluble polysaccharide which binds to soy protein.

2. The process of claim 1 further comprising clarifying juices, wines or beers by the treatment.

3. The process of claim 1 further comprising liquefying a polysaccharide containing process waste material by treatment an aqueous suspension of such material with said SPS-ase preparation.

4. The process of claim 1 further comprising treating an aqueous suspension of a process waste material selected from the group consisting of sugar beet pulp, pomace and remanence from production of soy milk.

5. The process of claim 1 further comprising treating fresh silage with a solution of said SPS-ase preparation.

* * * * *